United States Patent
Burtin

Patent Number: 6,098,207
Date of Patent: Aug. 8, 2000

[54] PROTECTIVE EYEWEAR

[76] Inventor: Mayme L. Burtin, 16163 Hwy. 64, Lebanon, Mo. 65536

[21] Appl. No.: 09/233,619

[22] Filed: Jan. 19, 1999

Related U.S. Application Data

[60] Provisional application No. 60/071,982, Jan. 20, 1998.

[51] Int. Cl.$^7$ ...................................................... A61F 9/02
[52] U.S. Cl. .................................. 2/431; 2/449; 351/158
[58] Field of Search ............................... 2/431, 426, 432, 2/442, 445, 448, 449, 440, 422, 452; 351/158

[56] References Cited

U.S. PATENT DOCUMENTS

| | | | |
|---|---|---|---|
| 2,920,327 | 1/1960 | Singer | 2/431 |
| 4,229,837 | 10/1980 | Solari | 2/431 |
| 4,527,291 | 7/1985 | Nussbickl | 2/450 |
| 4,547,909 | 10/1985 | Bell | 2/431 |
| 4,703,522 | 11/1987 | Schurle et al. | 2/432 |
| 4,810,080 | 3/1989 | Grendol et al. | 351/41 |
| 5,069,541 | 12/1991 | Holmes et al. | 351/86 |
| 5,321,442 | 6/1994 | Albanese | 351/44 |
| 5,422,684 | 6/1995 | Keller | 351/41 |
| 5,455,639 | 10/1995 | Magdelaine et al. | 351/47 |
| 5,528,320 | 6/1996 | Specht et al. | 351/106 |
| 5,642,177 | 6/1997 | Nishioka | 351/47 |
| 5,907,868 | 6/1999 | Schleger et al. | 2/431 X |

*Primary Examiner*—Peter Nerbun
*Attorney, Agent, or Firm*—Jonathan A. Bay

[57] ABSTRACT

Protective eyewear has a lens frame containing one or more lenses and temple arms or straps for attaching the eyewear to the head of a wearer. The protective eyewear also includes a brow guard. The brow guard attaches to the lens frame. The brow guard is configured to extend in one direction substantially between the temple arms (or straps) and, in a transverse direction, between spaced edges, one of which edges is disposed adjacent the lens frame, the other of which edges is extended toward the brow of the wearer. The brow guard incorporates a magnetic material for attracting and catching magnetically attractable particles such that the magnetic material assists eliminating the drift of such particles down in the gap between the lens frame and the wearer's brow. Magnetic side shields can be added to the protective eyewear or substituted in place of the magnetic brow guard.

18 Claims, 4 Drawing Sheets

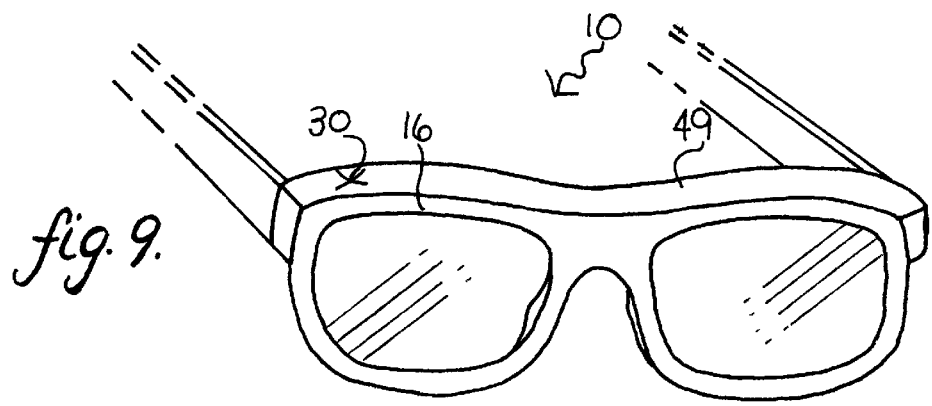
fig. 9.
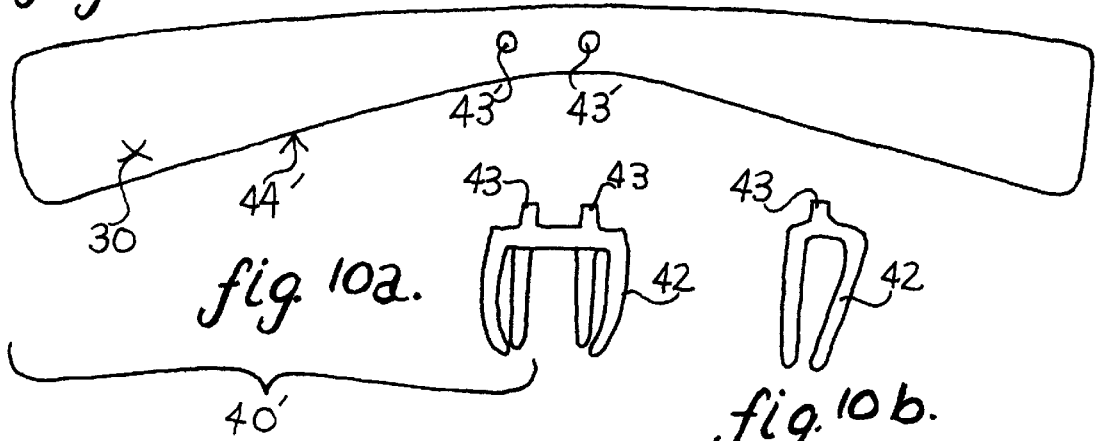
fig. 11.
fig. 10a.
fig. 10b.
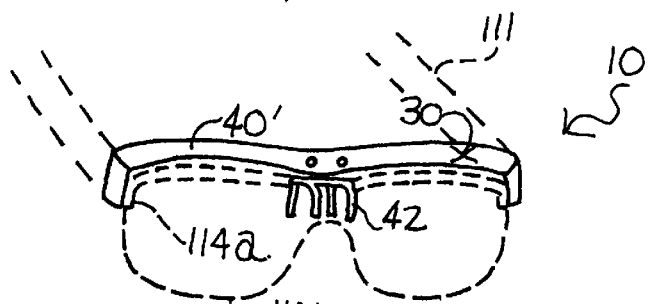
fig. 12a.
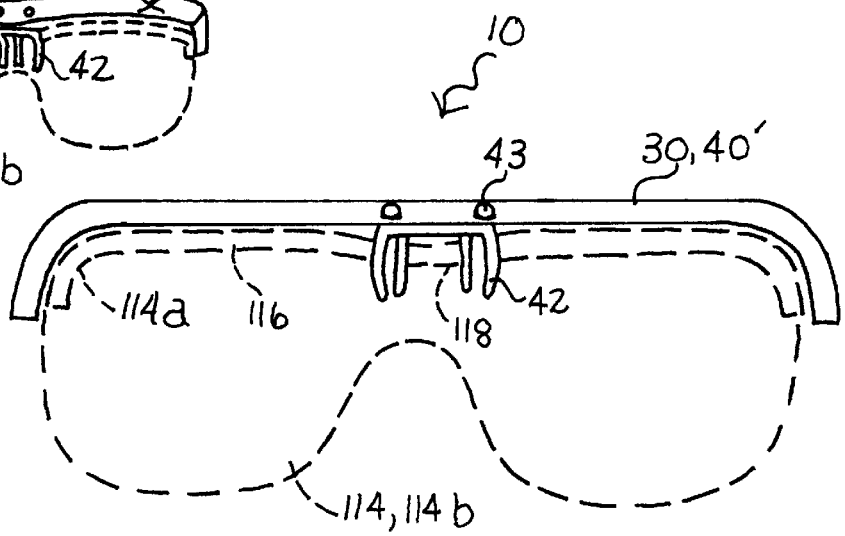
fig. 12b.

PROTECTIVE EYEWEAR

CROSS-REFERENCE TO PROVISIONAL APPLICATIONS(S)

This application claims the benefit of U.S. Provisional Application No. 60/071,982, filed Jan. 20, 1998.

BACKGROUND AND SUMMARY OF THE INVENTION

The invention relates to protective eyewear for use in home or industrial workshops and the like. In one of its versions, the protective eyewear in accordance with the invention comprises combining conventional safety spectacles—which are well known in the prior art—with an auxiliary brow guard which attaches to the frame of the conventional safety spectacles. One way of achieving attachment may include providing the auxiliary brow guard with a clip allowing clip-on attachment to the bridge of the spectacles. The auxiliary brow guard incorporates a permanent magnet material. The magnet material sets up a local magnetic field which attracts iron grit or particles given off by grinders or like shop tools, and pulls such iron particles onto the magnet material of the brow guard to secure it there.

The invention can be adapted to include magnetized side-shields and so on, for more fully surrounding the eyes with a magnetized iron-particle catcher. As previously mentioned, in some versions of the invention it has the format of a clip-on attachment allowing quick attachment and detachment to and from the frames of conventional prior art safety spectacles. In other versions of the invention is has the format of being more permanently integrated with the given frame(s) of the underlying safety spectacles.

Additional aspects and objects of the invention will be apparent in connection with the discussion further below of preferred embodiments and examples.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

FIG. 9 is a perspective view of an alternate embodiment of FIG. 2, in which the auxiliary brow guard is more permanently attached to the frames of the underlying spectacles;

FIGS. 10a, 10b and 11 comprise a set of views showing in a disassembled state one version of the auxiliary brow guard in accordance with the invention, wherein:

FIG. 10a is a front perspective view of the clip in isolation,

FIG. 10b is a side view of the clip of FIG. 10a, and

FIG. 11 is a plan view of the flexible permanent magnet material which is pinned or riveted to the clip of FIGS. 10a and 10b; and FIGS. 12a and 12b are a pair of views showing clip-on attachment of the auxiliary brow guard of FIGS. 10a through 11, onto a given frame of prior art safety spectacles, wherein;

FIG. 12a is perspective view thereof, and

FIG. 12b is an enlarged scale front elevational view thereof.

DETAILED DESCRIPTION OF THE PREFERRED EMBODIMENTS

Figure 1:
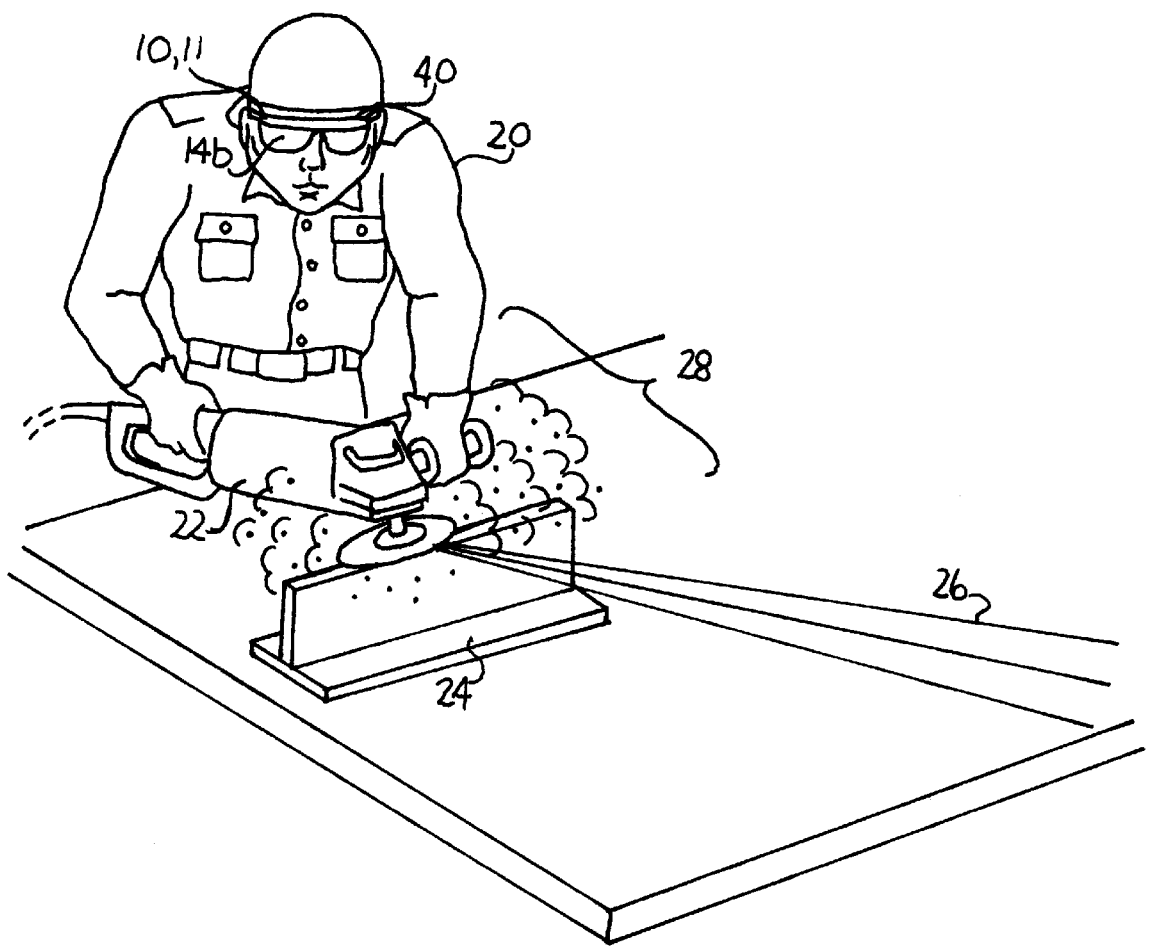
FIG. 1 is a perspective view of worker wearing a pair of protective eyewear in accordance with the invention, wherein the worker is depicted abrading a metal plate in a workshop to illustrate one operative use environment for the protective eyewear.

FIG. 1 shows a grinding operation typical in either a home or industrial workshop or job site environment. A worker 20 is shown operating a grinder 22 and abrading an edge of a steel (or ferritic material) workpiece 24. The grinding operation throws out many particles 26 and 28. The worker in FIG. 1 is wearing protective eyewear 10 in accordance with the invention. The eyewear 10 provides an enhanced measure of safety against eye injury from the particles.

In the drawing, the depiction of a grinding operation is shown to illustrate one example operative use environment for the invention. Other operative use environments include without limitation many other like metal-removing or -pulverizing, or metal-dust or -grit producing operations. These operations can take place in the home or in an industrial shop or wherever, including outdoors in open space job sites. Hence the depiction here of a grinding operation is included for illustrative purposes only and accordingly does not limit the invention just to grinding operations.

Figure 2:
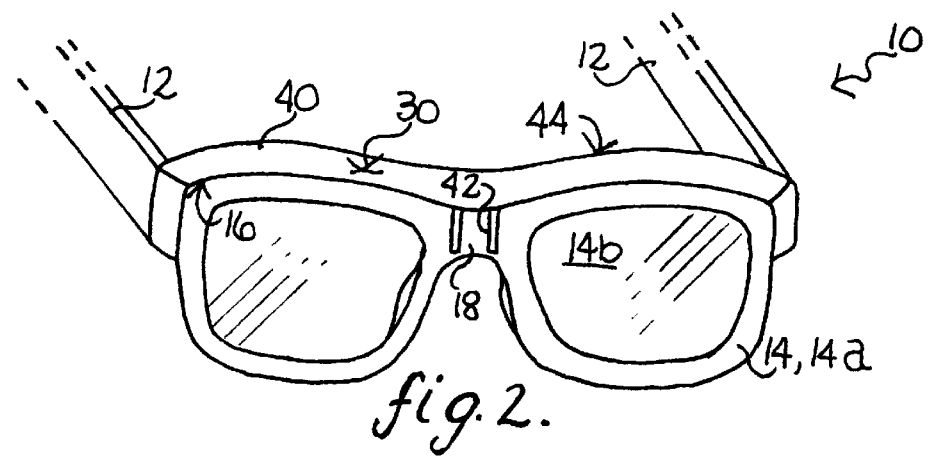
FIG. 2 is an enlarged perspective view of the protective eyewear of FIG. 1.

As shown by FIG. 2, the protective eyewear 10 in accordance with the invention comprises a combination of safety spectacles 11 and an auxiliary brow guard attachment 40. The safety spectacles 11 are representative of conventional prior art safety spectacles. Such safety spectacles (eg., 11) typically include a lens frame 14a for containing one or more lenses 14b and two temple arms 12 flanking the lens frame 14a for attaching the spectacles to the head of a wearer. The temple arms 12 may or may not be hinged to the frames 14a.

As the term is used in this written description, "spectacles" shall also include single lens spectacles 111 as shown by FIGS. 12a and 12b (including what are referred to in the industry as goggles, see, eg., U.S. Pat. No. 5,069,541—

Holmes et al. and/or U.S. Pat. No. 5,455,639—Magdelaine et al.). These kinds of spectacles or goggles 111 may have a relatively simple kind of lens frame 114a. That is, the lens frame 114a may comprise not much more than essentially an upper member or hanger support 116 (eg., compare to upper member 16 in FIGS. 2 and 9). This upper member 114a allows a singles lens 114b to be hung or suspended from it. Often times the single lens variety of safety spectacles or goggles 111 eliminate the temple arms 112 and attach to the head of the wearer more simply by means of an elastic strap (not shown in the drawings hereof). The invention can be used and incorporated with such single lens and/or strap-type safety spectacles/goggles and hence the invention is not limited merely to double lens and/or temple-arm type safety spectacles. The lens material is usually chosen from suitable shatterproof or impact resistant materials as popular among commercially available off-the-shelf models, including tempered glass or polycarbonate and the like.

FIG. 2 shows such spectacles 11 in which the lens frames 14a have a pair of lens sockets for encircling and retaining the lenses 114b. The lens sockets are joined by a nose bridge.

The foregoing aspects of the safety spectacles 11,111 of the inventive protective eyewear 10 are—without more—conventional in accordance with prior art safety spectacles. Generally, prior art safety spectacles are furthermore popular because they can easily include prescription lenses, they are reliably effective for warding off flying particles, and they can be comfortable to wear without sacrificing ventilation behind the frame/lens combination 14. Also, prior art safety spectacles are widely available, readily obtainable, and affordable.

One inventive aspect of the protective eyewear 10 of FIG. 2 is the following. The spectacles 11 have a brow guard 40 mated along an upper member 16 of the frame 14a. This upper member 16, more particularly, comprises the nose bridge as well as respective upper arc portions of the lens sockets that flank the nose bridge. The brow guard 40 incorporates a magnetic material 30. More preferably, the magnetic material of the brow guard 40 substantially takes the form of sheet-form flexible permanent magnet material. The sheet-form flexible permanent magnet material is shaped into a strip as shown. Sheetform flexible permanent magnet material is available from such commercial sources as, including without limitation, Magnetic Speciality, Inc., of Marietta, Ohio.

The quality of "rigidity" of sheet-form flexible permanent magnet material varies with the thickness of the gauge of the sheet. Very thin gauge sheet-form flexible permanent magnet material has virtually no inherent rigidity against sagging or drooping. In contrast, relatively thicker gauge sheet-form flexible permanent magnet material has sufficient inherent stability such that if supported cantilevered along one edge as shown in FIG. 2, it ought to self-support is opposite free edge from sagging or drooping down into an impractical position. However, the drooping or sagging quality of thin gauge sheet-form flexible permanent magnet material can offer some benefit. The brow guard 40 can effectively be formed effectively as a soft flap (not shown in the drawings, in which the brow guard 40 is depicted as a relatively rigid flap). That way, a soft flap of a brow guard 40 could extend such that it rests against the wearer's forehead (not shown). A soft flap of a brow guard 40 could almost form a loose seal with the wearer's forehead. The advantages that a seal would provide would weigh against the disadvantages of cutting back on ventilation behind the lenses 14b.

Figure 3A:
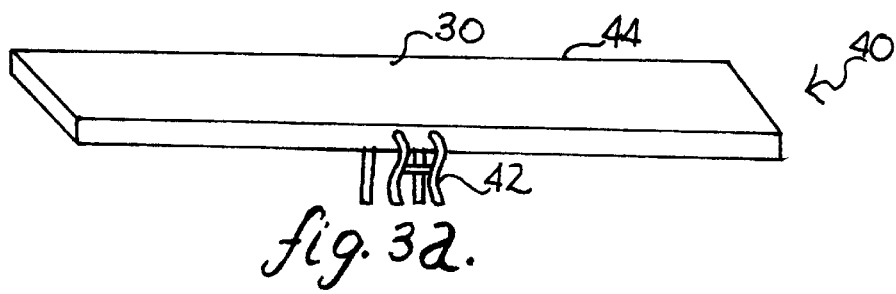
FIG. 3a is a perspective view of the inventive auxiliary brow guard of the protective eyewear of FIG. 2, as shown in isolation, which brow guard incorporates a flexible permanent magnet material.
Figure 3B:
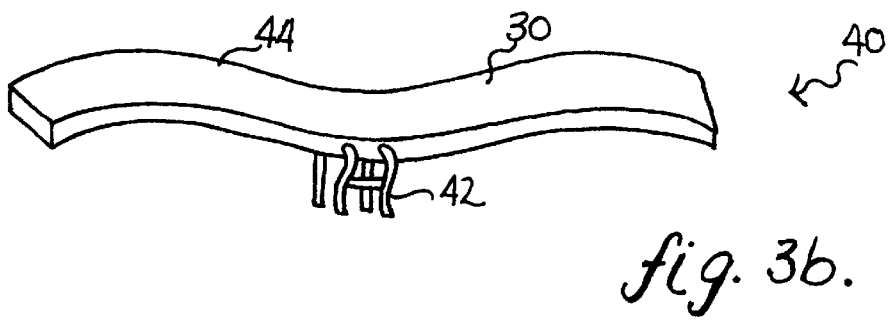
FIG. 3b is a perspective view of the brow guard of FIG. 3a, which is shown flexed.

FIGS. 3a and 3b show the magnetic brow guard 40 in a flat and flexed formats, respectively.

The FIG. 3a brow guard 40 is shown relaxed in a generally flat condition. The brow guard 40 includes a central clip 42 for attachment to the nose-bridge 18 of the frame 14a. In some lens frames (eg., see 114a in FIGS. 12a and 12b) the nose bridge portion 118 of the upper member 116 is not so much a distinct portion of the upper member 116 but more generally just a portion of the center of geometry of the upper member 116.

With reference back to FIG. 2, assembly of the brow guard 40 to the frame 10 optionally comprises the assembly steps of:

(i) flexing the brow guard strip 40 in the double-arch eyebrow shape shown (and, eg., as shown by FIG. 3b), (ii) attaching the clip 42 to the frame nose-bridge 18, and then perhaps (iii) adhering the brow guard 40 to the upper member 16 of the frame 14a with any suitable adhesive including rubber-based and/or acrylic-based adhesives which are known in the art for applications involving bonding to sheet-form flexible permanent magnets.

The FIG. 3b format of the brow guard 40 preferably can be formed or shaped such that the brow guard 40 rigidly holds the double-arch eyebrow shape as shown. It therefore can be attached and detached to and from the safety spectacles 11 in the same fashion as clip-on sunglasses. It is therefore preferred if the spectacle frame 14a is made of a ferritic (eg., magnetically attractable) material. That way, the magnetic attraction of the brow guard 40 to the upper member 16 would assist the nose-bridge clip 42 in retaining the brow guard 40 on the frame 14a.

Inventive aspects of the magnetic brow guard 40 will be more apparent with renewed reference back to FIG. 1. The worker 20 is grinding a metal workpiece 24 which also comprises at least some fractional portion of magnetically attractable material in the matrix of the workpiece material. The grinding operation is scattering waste-product particles 26 and 28 in many directions. One obvious safety hazard—an obvious one—includes the following. Relatively large particles 26 are capable of ricochet right back at the worker 20. The lenses 14b of the spectacles 11/eyewear 10 provide the obvious safeguard against the obvious hazard of such reflected particles 26:—the lenses 14b are shatterproof or at least impact resistant and simply deflect the ricochet particles harmlessly away (this is not shown).

An alternative safety hazard—one which might not be as obvious—includes the scattering of relatively minute grit particles 28. Such minute grit particles 28 do not so much ricochet as instead flutter and drift about in the air before eventually settling out. It is an inventive aspect of the protective eyewear 10 that the magnetic brow guard 40 provides an alternative safeguard against this alternative safety hazard.

It can be reckoned that, the spectacles 11 alone leave a gap between the upper member 16 of the frame 14 and the brow of the wearer. There is a risk that fluttering or drifting grit particles 28 can drift or float within the gap between the worker's brow and the frame 14a. Thereafter the grit particles 28 might land in the worker's eyes. When this happens, such grit particles 28 are likely to be hot. Such grit particles 28 are therefore likely to provoke violent discomfort if not injury. Hence the worker's eyes are at risk of injury. Also, the worker 20 might self-inflict harm upon him or herself with the grinder 22 (or whatever tool he or she may be handling) if the worker should jerk too carelessly when such a hot grit particle 28 lands in the eye.

In accordance with the invention, the magnetic brow guard 40 effectively filters out such magnetically attractable particles 28 that float through such sufficiently strong lines of magnetic force as to be attracted to and held to the magnet material. Hence the magnetic brow guard 40 pulls out the particles 28 that may try to drift or circulate within the gap between the worker's eyes and the lens frame 14a. Consequently the brow guard 40 provides safety against such grit particles 28 as sized on such a small scale as are likely to drift for a time before settling.

Figure 4:
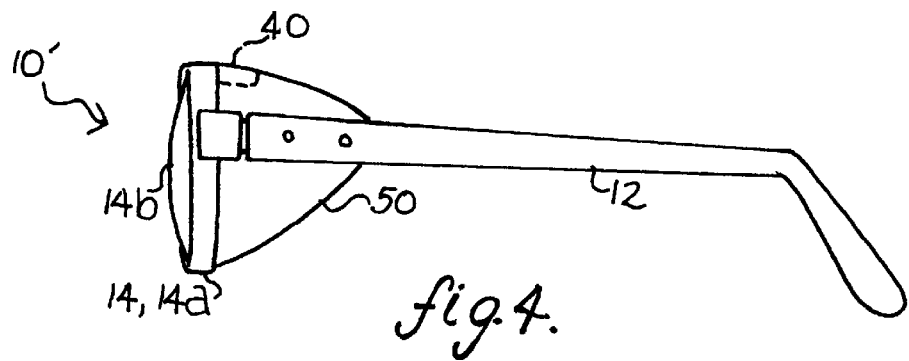
FIG. 4 is a side perspective view of an alternate version of protective eyewear in accordance with the invention, which is provided with side shields incorporating a permanent magnet material.

FIG. 4 shows a modification to and/or an alternate version of the protective eyewear 10' of FIG. 2. The FIG. 4 eyewear 10' includes side shields 50 (e.g., only near side shown by the view). Each side shield 50 is formed out of a patch of sheet-form flexible permanent magnet material. The side shields 50 provide comparable safety as the brow guards 40 do against drifting or fluttering grit particles 28, except that the side shields 50 filter out particles which approach the gap between the frames 14a and the worker's eyes from a side.

Other advantages of the inventive brow guard 40 and/or side shields 50 include the following. The sheet-form flexible permanent magnet material 30 can be cut by shears or perhaps heavy scissors. Thus a worker can modify the brow guard 40 such that an inside edge (indicated as 44 in the drawings) can be cut in a curve in to more closely wrap around or conform to the bulge of his or her forehead. While this is not shown in FIGS. 1 through 9, this is indeed shown by, for example, FIGS. 11, 12a and 12b. The sheet-form flexible permanent magnet material 30 clearly shows an inside edge 44' cut with a curve which would more closely wrap around or conform to the bulge of the forehead of the wearer. Curving the inside edge 44' this way minimizes the physical measure of the gap between the inside edge 44' and the brow of the wearer.

Each worker can personally shape or tailor the inside edge from straight 44 to shaped 44' to achieve a good if not best "fit" to his or her own brow, and most likely at least much better than the straight line edge 44 shown by FIG. 3a. Again, the brow guard 40 can effectively be shaped (see, eg., brow guard 40' of FIGS. 11 through 12b) with scissors or shears to close up or minimize any gap between the frame 14a, 140a and the forehead.

Moreover, the brow guard 40 is inexpensive and disposable. Therefore, after heavy use when much grit has accumulated on one, a given brow guard 40 can simply be discarded in favor for a fresh replacement. This eliminates the messy procedure of "wiping clean" any brow guard 40 to reduce its loading.

Figure 5:
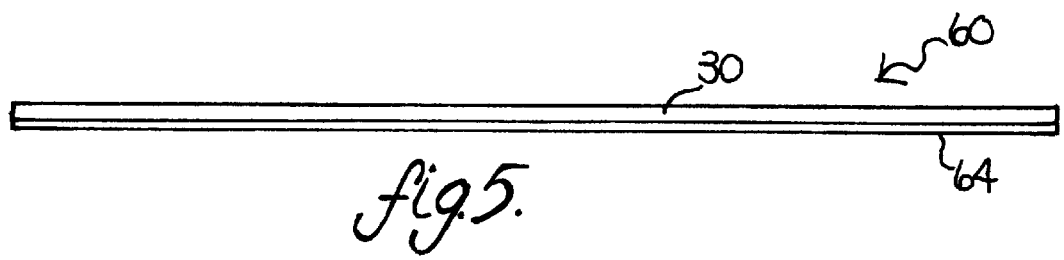
FIG. 5 is an elevational view of an edge of a composite material from which to form brow guards and/or side guards for the protective eyewear in accordance with the invention, wherein the composite material comprises a layer of flexible permanent magnet material bonded with a layer of a malleable material.

FIGS. 5 taken with 6 through 8 show various further versions 46–47 of magnetized brow guards and/or side shields for protective eyewear 10 in accordance with the invention. These further versions 46–48 are formed from a composite material 60, which is best shown by FIG. 5.

In FIG. 5, the composite material 60 comprises a layer of sheet-form flexible permanent magnet material 30 bonded to a layer of a malleable material 64 such as aluminum or the like. Aluminum has been chosen merely as one suitable material which desirably is sufficiently malleable to allow deformation by hand and yet retain the shape in which it is deformed. Many other materials would suffice for the purposes as aluminum presently does.

Figure 6:
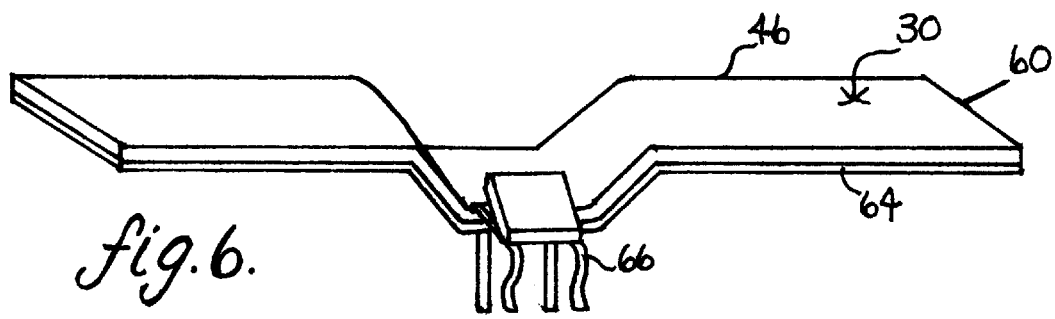
FIG. 6 is a perspective view of an auxiliary brow guard formed from the composite material of FIG. 5.
Figure 7:
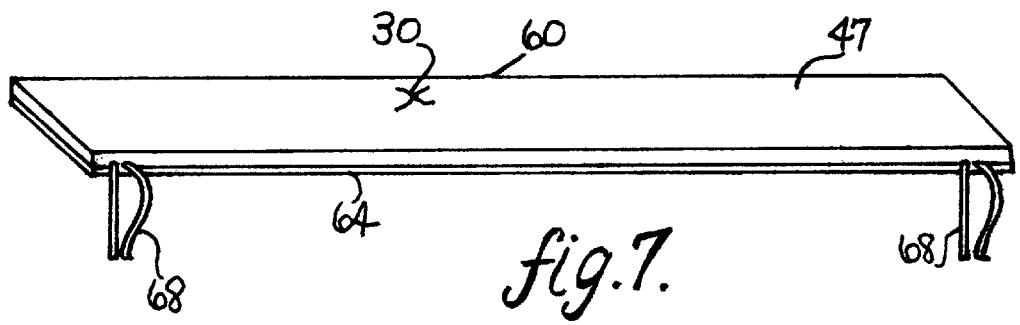
FIG. 7 is a perspective view comparable to FIG. 6 except showing another variant of the auxiliary brow guard thereof.

FIG. 6 shows a clip-on version 46 of the brow guard incorporating the composite material 60 shown by FIG. 5. The sheet-form flexible permanent magnet material 30 is situated as the exposed upper layer. The malleable (eg., aluminum) layer 64 is situated below. The brow guard 46 features a lever-actuated nose-bridge clip 66 as is known in the art of clip-on sunglasses and the like. Preferably the brow guard 46 is supplied to the end-user thereof in a flat condition, as shown by FIGS. 5 or 7. The end-user is given the opportunity to deform and bend the brow guard 46 into the shape he or she personally desires, such as the gull wing shape shown by FIG. 6.

FIG. 7 shows an alternate version 47 of a clip-on brow guard which is formed from the composite material 60 of FIG. 5. The FIG. 7 brow guard 47 is also shown in a flat condition as preferably sold and distributed to the ultimate end-user thereof. The end user (eg., the ultimate wearer) is expected to bend the brow guard 47 into his or her personally preferred desired shape. This FIG. 7 version 47 of the brow guard includes a pair of widely spaced clips 68 which allow removable attachment to the frames 14a (the attachment to frames 14a not shown, but generally cross-reference to FIGS. 2, 9, and 12a, 12b) near where the hinges for the temples 12 are (again refer to FIGS. 2, 9 or 12a and 12b).

Figure 8:
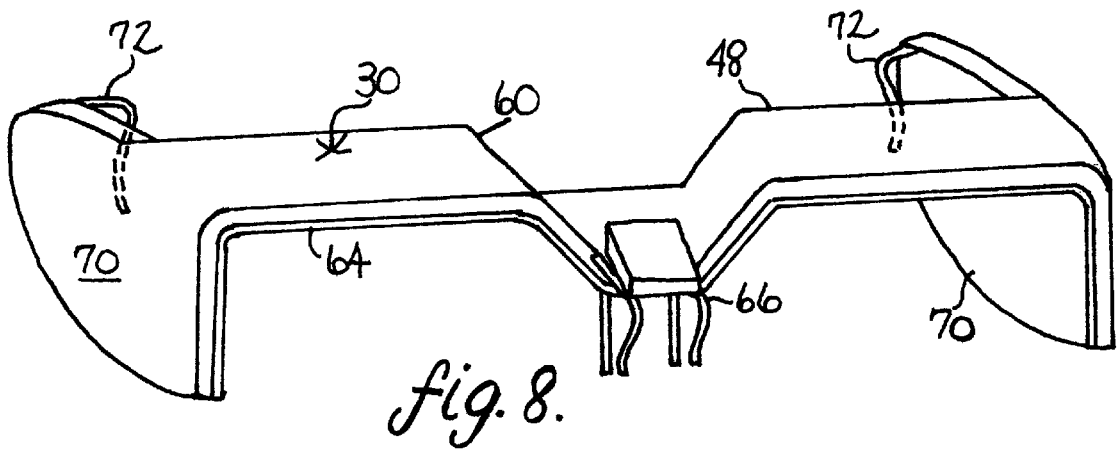
FIG. 8 is a perspective view of still another version of the auxiliary brow guard in which side shields are included as well.

FIG. 8 shows another version 48 of a clip-on brow guard for protective eyewear 10 in accordance with the invention. The FIG. 8 brow guard 48 is comparable to the FIG. 6 brow guard 46 except that the FIG. 8 version includes opposite left and right enlarged lobes or turned-down flaps 70. The lobes 70, when bent down from the plane of the central span 48, are sufficiently disposed to define side shields. The side shields (e.g., lobes or flaps) 70 thereof further include rear hooks 72 to loop over the temples 12 (this is not shown, but generally cross-reference to any of FIGS. 2, 9 or 12a and 12b) of the eyewear. The rear hooks 72 enhance stability.

Hence, if a user is given a single clip-on brow guard like any of attachments 40, 40', 46, 47 or 48 or the like, then such a user of conventional prior art safety spectacles 11,111 can convert the spectacles 11,111 to protective eyewear 10 in accordance with invention. This desirably provides grit-filtering magnetic fields across the eyebrow of the wearer and/or along the lateral sides of the frames 14. Such clip-on attachments (for example, 40, 40', 46, 47 and 48) are affordable and disposable, and thus are optimum for scheduled replacement after each reaches the end of its useful life because of grit-loading or the like.

The foregoing discussion of a magnetized brow guards 40, 40', 46, 47 or 48 as well as side shields 50 and 70 in accordance with the invention does not expressly describe the brow guards and/or side shields in any other terms besides that they are predominantly an after-market add-on for attachment to conventional prior art spectacles 11 or 111.

On the contrary, however, major objects of the invention can be achieved even if the brow guards 40, 40', 46, 47 or 48 as well as side shields 50 and 70 are integrated with the frames 14,114 of the underlying spectacles 11,111. For example, FIG. 9 shows sheet-form permanent magnet material 30 permanently attached to the frame upper member 16 of eyewear 10. This FIG. 9 form of the eyewear 10 and magnetic brow guard 49 eliminates the clip 42,66 shown by other drawings.

FIGS. 10a through 12b show production of a brow guard 40'. The clip 42 has a pair of pins 43. The sheet-form magnetic material 30 has a pair of corresponding holes 43' in which the pins 43 are inserted. The heads of the pins 43 are mushroomed out as shown by FIG. 12b or 12a. In effect, the clip 42 is sort of riveted to the sheet-form magnetic material 30. Other ways of joining the clip 42 and sheet-form magnetic material 30 are routinely known and suitable for the purposes of the present invention.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. Protective eyewear comprising:

a lens frame containing one or more lenses and having an upper frame member absent from which is any practical brow-ward shelf providing shielding like a brow guard, means for attaching the eyewear to the head of a wearer;

a replaceable, sheet-form magnetic flap for attaching to the lens frames, the flap having upper and under sides and extending laterally between opposite lateral edges and trans-laterally between an outboard edge and an inboard edge, the under side having an outboard margin for perching on and securing to the upper frame member of the lens frame by virtue of the under side's outboard margin being associated with releasable securing means for securing the flap and upper frame member in an alignment such that the flap's inboard edge is extended brow-ward to close up a gap between the inboard edge and the wearer's brow, which thereby has the flap cantilevered as a shielding shelf or brow guard, wherein the magnetic flap incorporates a magnetic material for attracting and catching magnetically attractable particles on the upper side for thereby assisting elimination of the drift of such particles down in said gap between the inboard edge and the wearer's brow; whereby the releasable securing means facilitates replacement of the flap with another if the upper side gets overloaded.

2. The protective eyewear of claim 1 further comprising a pair of side shields for attaching to one or both of the lens frame and attaching means;

the side shields having an outboard edge which is disposed adjacent the lens frame, and extending toward a spaced away inboard edge such that the side shields cover at least portions of the wearer's temples;

wherein the side shields incorporate a magnetic material for attracting and catching magnetically attractable particles such that the magnetic material thereby assists eliminating the drift of such particles across such gap defined between the side shields' inboard edges and the wearer's temples.

3. The protective eyewear of claim 1 wherein the magnetic material comprises sheet-form, flexible permanent magnet material.

4. The protective eyewear of claim 3 wherein the magnetic material further comprises a layer of sheet-form malleable material mated to the sheet-form flexible permanent magnet material, the malleable material allowing shaping of the sheet-form flexible permanent magnet material.

5. The protective eyewear of claim 3 wherein:

the lens frame upper frame member has a portion near its center which defines a nose bridge portion;

the releasable securing means includes a resilient clip allowing clip-on, frictional-gripping retention attachment and clip-off detachment to and from such nose bridge portion of the lens frame.

6. The protective eyewear of claim 1 wherein the attaching means comprises one of strap(s) and temple arms.

7. The protective eyewear of claim 1 wherein the lens frame comprises a pair of lens sockets for containing a pair of lenses of shatterproof material, and the upper frame comprises a nose bridge and flanking upper arc portions of the lens sockets.

8. A combination of safety spectacles and an auxiliary magnetic brow guard comprising:

safety spectacles having a lens frame containing one or more lenses and having temple arms for holding the spectacles to the head of a wearer, the lens frame having an upper frame member absent from which is any substantial brow-ward shelf providing shielding like a brow guard;

a sheet-form auxiliary magnetic brow guard for attaching to the safety spectacles, the brow guard having upper and under sides and extending laterally substantially between the temple arms and extending trans-laterally between spaced inboard and outboard edges, the under side having an outboard margin for perching on and securing to the upper frame member of the lens frame by virtue of the under side's outboard margin being associated with releasable securing means for securing the auxiliary brow guard and upper frame member in an alignment such that the auxiliary brow guard's inboard edge is extended brow-ward to close up a gap between the inboard edge and the wearer's brow, which thereby has the auxiliary brow guard cantilevered as a shielding shelf or actual brow guard;

wherein the auxiliary brow guard incorporates a magnetic material for attracting and catching magnetically attractable particles on the upper side such that the magnetic material thereby assists eliminating the drift of such particles down in said gap between the inboard edge and the wearer's brow; whereby the releasable securing means facilitates replacement of the auxiliary brow guard with another if the upper side gets overloaded.

9. The combination of claim 8 wherein:

the lens frame upper frame member has a portion near its center which defines a nose bridge portion;

the releasable securing means includes a resilient clip allowing clip-on, frictional-gripping retention attachment and clip-off detachment to and from such nose bridge portion.

10. The combination of claim 8 wherein the magnetic material comprises sheet-form, flexible permanent magnet material.

11. The combination of claim 10 wherein the magnetic material further comprises a layer of sheet-form malleable material mated to the sheet-from flexible permanent magnet material, the malleable material allowing shaping of the sheet-form flexible permanent magnet material.

12. The combination of claim 8 further comprising a pair of side shields for attaching to the spectacles;

the side shields having an outboard edge which is disposed adjacent the lens frame, the side shields extending toward a spaced away inboard edge such that the side shields cover at least portions of the wearer's temples;

wherein the side shields incorporate a magnetic material for attracting and catching magnetically attractable particles and to thereby assist eliminating the drift of such particles across such gap defined between the side shields' inboard edges and the wearer's temples.

13. The protective eyewear of claim 1 wherein the releasable securing means comprises an adhesive on the under side's outboard margin which sticks to the upper frame member when originally pressed upon.

14. The protective eyewear of claim 13 wherein release of the adhesive is achieved, in order to replace the flap, by pulling the flap and lens frame apart.

15. The protective eyewear of claim 13 wherein the sheet-form flap comprises a thin scissorable material that permits sizing by simple use of scissors, and the flap is provided oversized such that a wearer can custom trim the inboard edge in order to get a more closely closed up gap between the trimmed inboard edge and wearer's brow.

16. The combination of claim 8 wherein the releasable securing means comprises an adhesive on the under side's outboard margin which sticks to the upper frame member when originally pressed upon.

17. The combination of claim 16 wherein release of the adhesive is achieved, in order to replace the auxiliary brow guard, by pulling the auxiliary brow guard and lens frame apart.

18. The combination of claim 8 wherein the sheet-form auxiliary brow-guard comprises a thin scissorable material that permits sizing by simple use of scissors, and the auxiliary brow-guard is provided oversized such that a wearer can custom trim the inboard edge in order to get a more closely closed up gap between the trimmed inboard edge and wearer's brow.

* * * * *